(12) United States Patent
Pfefferle et al.

(10) Patent No.: US 8,603,407 B2
(45) Date of Patent: Dec. 10, 2013

(54) CATALYTIC ISOBUTANE ALKYLATION

(75) Inventors: William C. Pfefferle, Madison, CT (US); Shahrokh Etemad, Trumbull, CT (US)

(73) Assignee: Precision Combustion, Inc., North Haven, CT (US)

( * ) Notice: Subject to any disclaimer, the term of this patent is extended or adjusted under 35 U.S.C. 154(b) by 704 days.

(21) Appl. No.: 11/726,106

(22) Filed: Mar. 21, 2007

(65) Prior Publication Data
US 2008/0234528 A1    Sep. 25, 2008

(51) Int. Cl.
*B01J 19/26* (2006.01)
*C07C 2/62* (2006.01)

(52) U.S. Cl.
USPC ........... 422/239; 422/198; 422/202; 422/203; 422/211; 422/222; 585/709; 585/720; 585/721; 585/722; 585/923

(58) Field of Classification Search
USPC ................ 422/239, 198, 202, 203, 211, 222; 585/720, 922, 923, 954, 709, 721, 722
See application file for complete search history.

(56) References Cited

U.S. PATENT DOCUMENTS

| | | | |
|---|---|---|---|
| 3,893,942 A * | 7/1975 | Yang .............................. | 585/722 |
| 4,008,291 A | 2/1977 | Zabransky et al. | |
| 5,583,240 A * | 12/1996 | Asher et al. ...................... | 554/98 |
| 6,238,815 B1 | 5/2001 | Skala et al. | |
| 6,838,064 B2 * | 1/2005 | Sakai ............................ | 422/211 |
| 6,977,064 B1 * | 12/2005 | Adris et al. .................... | 422/196 |
| 2004/0229752 A1 * | 11/2004 | Long et al. ..................... | 502/303 |
| 2005/0166456 A1 * | 8/2005 | Brundage et al. ............. | 48/198.7 |
| 2005/0245782 A1 * | 11/2005 | Pfefferle ........................ | 585/722 |
| 2005/0250972 A1 | 11/2005 | Pfefferle | |
| 2005/0256358 A1 * | 11/2005 | Wang et al. .................... | 585/709 |
| 2007/0270623 A1 * | 11/2007 | Merrill .......................... | 585/446 |

FOREIGN PATENT DOCUMENTS

WO    WO 02/074701    9/2002

OTHER PUBLICATIONS

V. Meille, "Review on Methods to Deposit Catalysts on Structured Surfaces," Applied Catalysis A: General, 315 (2006), 1-17.*
Meille, "Review on Methods to Deposit Catalysts on Structured Surfaces," in Applied Catalysis A: General, 315 (2006), 1-17.*
Edgar, et al., "Process Control" in Perry's Chemical Engineer's Handbook, McGraw-Hill, 7th ed., 1997, R. H. Perry and D. W. Green, ed., available on-line Mar. 1, 2001 at www.knovel.com.*

* cited by examiner

*Primary Examiner* — In Suk Bullock
*Assistant Examiner* — Bradley Etherton
(74) *Attorney, Agent, or Firm* — Robert L. Rispoli

(57) ABSTRACT

A novel catalytic reactor is provided for controlling the contact of a limiting reactant with a catalyst surface. A first flow vessel defines an interior surface and an exterior surface, and the interior surface has a catalyst deposited on at least a portion thereof. A second flow vessel is positioned within the first flow vessel and the second flow vessel defines a porous surface designed to deliver a fluid uniformly to at least a portion of the interior surface of the first flow vessel.

8 Claims, 2 Drawing Sheets

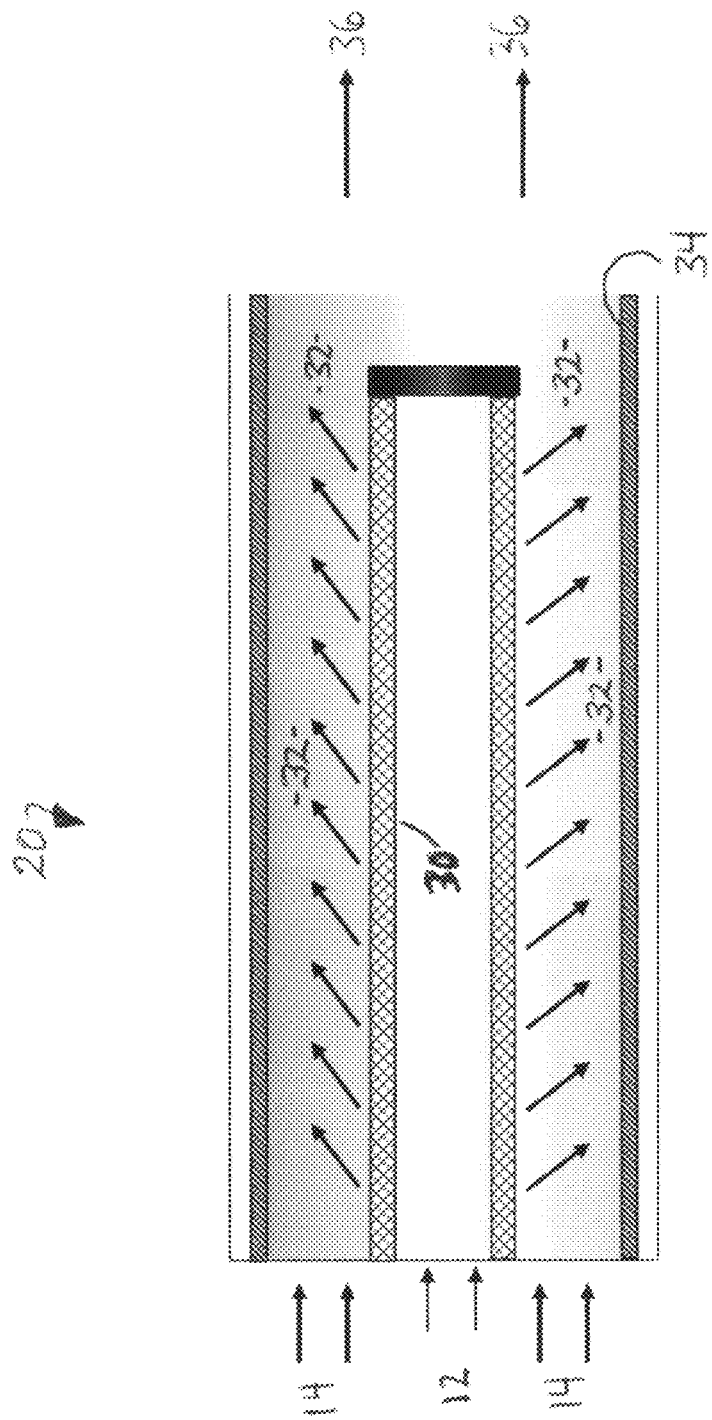

CATALYTIC ISOBUTANE ALKYLATION

BACKGROUND OF THE INVENTION

1. Field of the Invention

The present invention relates to a method for catalytic isobutane alkylation. More particularly, the present invention is directed to a catalytic isobutane alkylation process that is advantageous for the alkylation of isobutane or benzene, as well as other compounds.

2. Description of the Related Art

Isobutane alkylation by reaction with an olefin is an important refinery process producing a high-octane alkane hydrocarbon product used to produce high-octane gasoline of low aromatic content. Commercial alkylation processes rely on use of either hydrogen fluoride or sulfuric acid catalyst systems. Unfortunately, both systems pose both environmental and safety hazards.

Hydrogen fluoride is an extremely toxic gas and even very small leaks are both a potentially lethal hazard for plant personnel and an area-wide health hazard. On the other hand, sulfuric acid is a burn hazard and the organics-contaminated spent acid is a toxic material that, if burned, creates sulfur oxide fumes. Consequently, it is an object of the present invention to provide a more environmentally benign alkylation process that could be used for alkylation of butane and aromatic compounds such as benzene. It is another object of the present invention to provide solid catalyst systems for use in heterogeneous fixed bed reactors.

With the development of synthetic zeolites, solid catalysts with a high activity for isobutane alkylation have become available. As is known in the art, zeolitic catalysts active for commercial alkylation processes also are active for olefin polymerization, a reaction that reduces alkylate octane and can produce high molecular weight polymers. Further, because the olefin polymerization reaction tends to be favored over the desired alkylation reaction, a very high ratio of isobutane-to-olefin must be used to reduce the probability of olefin-to-olefin polymerization.

In commercial alkylation processes, polymer formation produces sludge; however, it is merely a nuisance. In contrast, in an alkylation process employing a solid catalyst, polymer formation can block the active sites thereby requiring catalyst regeneration. Moreover, with both conventional and zeolite catalysts, the required high isobutane-to-olefin ratio increases operating cost because the unreacted isobutane must be recovered from the product stream and recycled. Unfortunately, polymer formation on a fixed-bed zeolitic catalyst results in catalyst deactivation in an economically unacceptable short time if operated at the isobutane-to-olefin ratio used in the commercial processes.

Accordingly, it is an object of the present invention to provide a catalytic isobutane alkylation process that overcomes these and other drawbacks associated with known commercial alkylation processes. It is yet another object of the present invention to provide a catalytic isobutane alkylation process that is advantageous regardless of the compound to be alkylated.

DESCRIPTION OF THE INVENTION

It has now been found that using a unique reactor design together with controlled addition of olefin, a nominally constant low olefin concentration can be maintained at the catalyst surface. In isobutane alkylation, for example, the effective isobutane-to-olefin surface ratio can even be greater than a thousand-to-one at feed ratios of ten or twenty-to-one.

Polymer formation on a fixed-bed alkylation catalyst can be reduced to an acceptable level allowing the use of known solid alkylation catalysts at isobutane-to-olefin ratios acceptable in commercial isobutane alkylation. The present invention allows operation even at isobutane-to-olefin ratios lower than those required in current commercial processes. It has now been found that high isobutane ratios on the catalyst surface do not require high isobutane ratios for the feed streams. Although described in terms of isobutane alkylation, the method of the present invention is generic and applies to alkylation of any compound with an olefin and to any reaction where it is desirable to limit concentration of a reactant on a catalytic surface.

BRIEF DESCRIPTION OF THE DRAWINGS

FIG. 2 provides a cross section of the encircled area noted by the designation "2-2" on FIG. 1.

DETAILED DESCRIPTION OF THE INVENTION

Figure 1:
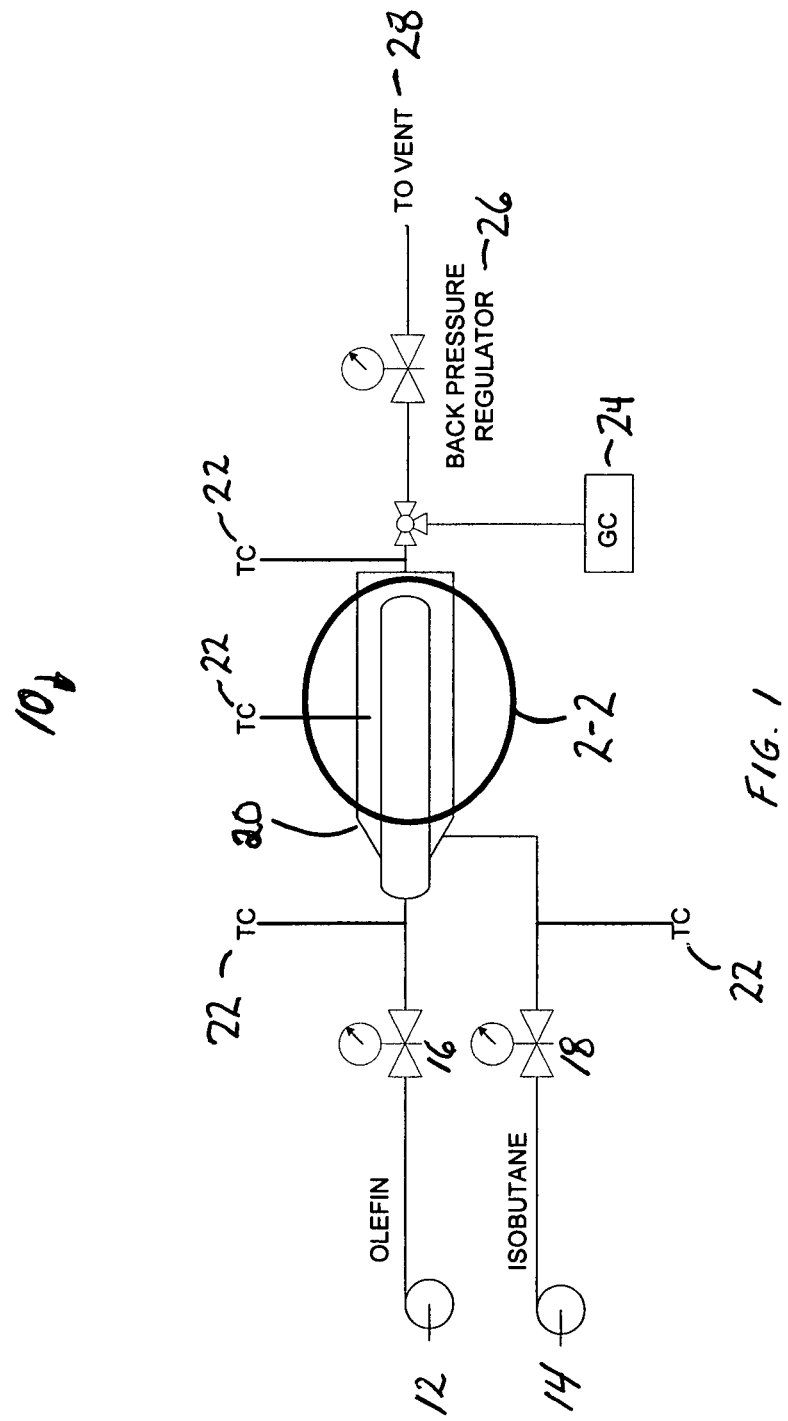
FIG. 1 provides a schematic of an isobutane alkylation system according to the present invention.

Isobutane alkylation system 10 according to the present invention for the alkylation of isobutane is depicted in FIG. 1. System 10 comprises an olefin feed 12 and an isobutane feed 14 controlled by respective flow regulators 16 and 18. The catalytic isobutane alkylation process occurs inside catalytic reactor 20, which reactor is further described with reference to FIG. 2. Four thermocouples 22 and a sample gas chromatograph 24 collect data for further evaluation of the catalytic isobutane alkylation process. Isobutane alkylation system 10 further comprises back pressure regulator 26 and then the products are passed to vent 28.

Catalytic reactor 20, as shown in FIG. 2, comprises a porous metal tube 30 that delivers the uniform flow of olefin 12 into the interior 32 of a catalyst coated outer tube 34 through which passes the flow of isobutane 14. Olefin 12 is passed into the porous metal tube 30 at a rate such that the olefin surface concentration at catalyst coated outer tube 34 surface is maintained at a high isobutane-to-olefin ratio. By controlling the olefin feed rate into the porous tube, olefin is injected at a uniform rate over the length of the tube such that mass transfer of olefin to the catalyst surface is limited to a value at which rapid catalytic reaction of olefin with isobutane limits olefin concentration to a desired level. The overall feed rate isobutane to olefin ratio is thus a function of reactor length determined by the cumulative production of alkylate 36.

In the embodiment of the present invention described herein, the term porous tube includes any device for flowing a reactant uniformly into contact with a catalyst surface at a controlled rate. Flat plate designs may be used. The design of FIG. 2 may be used for partial oxidation reactions wherein the flow of oxygen is limited on the surface of an oxidation catalyst to limit heat release. Reaction temperature may be controlled by backside cooling of the reactor in exothermic reactions. For endothermic reactions, reaction temperature can be maintained by backside heating.

Although the invention has been described in considerable detail with respect to the catalytic alkylation of isobutane, it will be apparent that the invention is capable of numerous modifications and variations, apparent to those skilled in the art, without departing from the spirit and scope of the invention.

The invention claimed is:

1. A catalytic isobutane alkylation reactor with reduced polymer formation on a fixed-bed alkylation catalyst comprising:
   a) an outer tube defining an outer tube interior surface and an outer tube exterior surface;
   b) an alkylation catalyst deposited on at least a portion of the outer tube interior surface defining a catalyst surface; and
   c) a porous metal tube positioned within the outer tube defining a porous metal tube interior surface and a porous metal tube exterior surface and providing a uniform flow rate over the length of the porous metal tube from the porous metal tube exterior surface to the outer tube interior surface;
   d) wherein under operative conditions when passing a feed of isobutane between the porous metal tube exterior surface and the outer tube interior surface and when passing a feed of olefin into the porous metal tube, an olefin surface concentration at the catalyst surface is maintained at an isobutane-to-olefin ratio greater than 50 times the isobutane-to-olefin ratio of the feeds of isobutane and olefin.

2. The catalytic reactor of claim 1 wherein the alkylation catalyst comprises a zeolite.

3. The catalytic reactor of claim 1 wherein the alkylation catalyst comprises a precious metal.

4. The catalytic reactor of claim 1 wherein the alkylation catalyst comprises platinum.

5. The catalytic reactor of claim 3 wherein the alkylation catalyst comprises rhodium.

6. The catalytic reactor of claim 1 wherein the outer tube exterior surface is in contact with a heat transfer fluid.

7. The catalytic reactor of claim 1 further comprising a flow regulator to control the flow of olefin.

8. The catalytic reactor of claim 1 wherein under operative conditions at a feed ratio of isobutane-to-olefin of 10/1 or 20/1, the isobutane-to-olefin ratio at the catalyst surface is greater than 1,000/1.

* * * * *